(12) United States Patent
Stenzel (10) Patent No.: US 8,042,373 B2
(45) Date of Patent: *Oct. 25, 2011

(54) METHOD AND APPARATUS FOR REDUCING A STENT

(75) Inventor: Eric B. Stenzel, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,614

(22) Filed: Feb. 22, 2010

(65) Prior Publication Data

US 2010/0143526 A1 Jun. 10, 2010

Related U.S. Application Data

(63) Continuation of application No. 11/137,638, filed on May 25, 2005, now Pat. No. 7,681,430.

(51) Int. Cl.
*B21D 41/00* (2006.01)
(52) U.S. Cl. ......................................................... 72/402
(58) Field of Classification Search .................... 72/402; 29/508, 517

See application file for complete search history.

(56) References Cited

U.S. PATENT DOCUMENTS

| 5,836,952 | A | 11/1998 | Davis |
|---|---|---|---|
| 6,178,802 | B1 | 1/2001 | Reynolds |
| 6,618,921 | B1 | 9/2003 | Thornton |
| 6,769,161 | B2 | 8/2004 | Plessel et al. |
| 6,823,576 | B2 | 11/2004 | Austin |
| 7,316,148 | B2 | 1/2008 | Asmus et al. |
| 2003/0070469 | A1 | 4/2003 | Kokish |
| 2004/0260379 | A1 | 12/2004 | Jagger et al. |
| 2005/0033404 | A1 | 2/2005 | Eidenschink |
| 2005/0229670 | A1 | 10/2005 | Perreault |
| 2006/0100689 | A1* | 5/2006 | Pryor .......................... 623/1.12 |
| 2006/0216404 | A1 | 9/2006 | Seyler et al. |

FOREIGN PATENT DOCUMENTS

| WO | 2006050425 A2 | 5/2006 |
|---|---|---|
| WO | 2006050425 A3 | 8/2007 |

\* cited by examiner

*Primary Examiner* — Edward Tolan
*Assistant Examiner* — Mohammad I Yusuf
(74) *Attorney, Agent, or Firm* — Seager Tufte Wickhem LLC (57) ABSTRACT

A medical device crimping system comprises a crimper and a plurality of protective strips. The crimper defines a crimping iris, which has an open state and a closed state. In the open state the cross-sectional area of the crimping iris is greater than in the closed state. The plurality of protective strips extend longitudinally through the crimping iris. Each of the strips is radially offset from one another. The strips protect the stent from direct contact with the crimping blades of the crimper.

19 Claims, 7 Drawing Sheets

METHOD AND APPARATUS FOR REDUCING A STENT

CROSS-REFERENCE TO RELATED APPLICATIONS

This application is a continuation of U.S. application Ser. No. 11/137,638, filed May 25, 2005 and entitled "METHOD AND APPARATUS FOR REDUCING A STENT."

BACKGROUND OF THE INVENTION

1. Field of the Invention

The present invention relates generally to stents, stent loading, stent contracting and stent delivery systems and their respective methods of use. Some embodiments of the invention are more specifically directed to stent loading and crimping systems which are configured to minimize cross-contamination.

2. Description of Related Art

A stent is a generally tubular device that is used to support a bodily lumen. A stent is typically delivered to a desired bodily location via a catheter. Often the stent is loaded onto a portion of the catheter, such as a balloon or other region of the catheter shaft. In some stent delivery systems the stent is crimped to the catheter in order to minimize the profile of the stent on the catheter and to prevent undesired movement of the stent relative to the catheter shaft.

A number of techniques for loading and contracting a stent to a catheter shaft or balloon are used. One such technique that is commonly used involves hand crimping the stent to the balloon. A stent is placed over an uninflated balloon and then squeezed with the fingers until the stent is in intimate contact with the uninflated balloon. The technique is highly operator dependent and can affect stent profile and stent placement with respect to the balloon and radiopaque markers. It can also affect the dilatation length of the stent and lead to pinching of the balloon.

Other techniques for crimping stents involve the use of mechanical devices for crimping stents. Mechanical stent crimpers have been disclosed in a number of patents including U.S. Pat. Nos. 6,387,118; 6,108,886; 6,092,273; 6,082,990; 6,074,381; 6,063,102 and 5,992,000. Mechanical stent crimpers have also been disclosed in a number of copending, commonly assigned patent applications including U.S. application Ser. Nos. 09/401467, 09/401213, 09/404986 and 09/401218. The entire content of each of the above patents and applications is incorporated herein by reference.

In many current stent loading operations particularly those involving self-expanding nitinol or shape memory stents the stent is dipped or sprayed with liquid nitrogen or other cooling agent in order for the stent to achieve a martensitic state. While in the martensitic state the stent is constrained via a crimper or other reducing device. In some cases the crimper comprises an adjustable iris through which the stent is advanced in order to uniformly reduce or compress the stent about its circumference. An example of an iris type stent crimper is described in U.S. Pat. No. 6,360,577, the entire content of which is incorporated herein by reference. Typically, a mandrel or push rod is utilized to drive the stent through the closed iris into a stent delivery mechanism such as a catheter.

Many current stent designs, including balloon expandable, self-expanding and hybrid expandable stents, are configured for the delivery of one or more therapeutic agents or drugs to a location within a body lumen or vessel. In many instances the drug or drugs are carried by the stent in the form of one or more coatings on the stent's surface. Stent loading and/or crimping systems which apply a radially constrictive force directly to the stent through one or more teeth, blades, etc. may adversely affect the drug coating of a stent during the crimping and/or loading process. Furthermore, contact between the crimping blades and the stent may result in some amount of the drug coating being removed from the stent and deposited on the crimping head. This residual amount of drugs may inadvertently be deposited on other stents subsequently crimped resulting in cross-contamination of the stent systems.

In light of the above there is a need to provide stent reducing/loading systems with the capability to reduce the diameter of a stent, particularly a drug coated stent, without direct contact of the stent by the crimping head.

All U.S. patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is particularly concerned with the crimping and otherwise reducing in size of stents, including drug delivery or coated stents of any configuration or expansion type, including inflation expandable stents, self-expanding stents, hybrid expandable stents, etc. For the purpose of this disclosure, it is understood that the term 'stent' includes stents, stent-grafts, grafts, vena cava filters, expandable supports, and other implantable medical devices for luminal support. It is also understood that the term 'crimping' refers to a reduction in size or profile of a stent and 'crimper' refers to devices for accomplishing such reduction in size or profile of a stent.

The present invention is embodied in a variety of forms. In at least one embodiment the invention is directed to a stent reducing and/or loading mechanisms such as stent crimpers and associated reducing and loading tools. In some embodiments a crimper comprises a crimping head, which defines the iris opening, through which the stent is placed prior to reducing. The iris opening has a variable diameter and may be adjusted between an open diameter and a closed diameter.

Positioned at each end of the crimper is a reel or spool, which contains a strip of protective material that extends through the iris from one spool to the other. In some embodiments the crimping assembly comprises at least two sets of opposed spools.

In at least one embodiments the assembly comprises three sets of spools to provide three strips of protective material. In at least one embodiment each strip is offset tangentially by about 120° within the iris channel.

The strips of protective material are distributed about the stent in such a manner so as to provide the stent with a protective layer or sheath which prevents direct contact of the crimping blades against the stent.

In some embodiments, positioned at each end of the crimper, between the spools and the crimping head, are one or more sheath forming plungers. In at least one embodiment each plunger defines an engagement surface or jaw which is constructed and arranged to bias a given strip toward the stent. Each of the jaws are constructed and arranged to apply a radially inward force on the strip of sheath material which is adjacent to each jaw. Each jaw is configured to move from an open or relaxed position to a more radially inward closed position. In the closed position the jaw will act to bias the strip of sheath material in a more radially inward manner so as to bring the strip into contact with the a stent positioned within the iris.

In some embodiments the strips of sheath material are sized and arranged such that when the jaws are in the closed position the adjacent strips, in effect, form a continuous "sheath" of strip material about the stent being crimped.

In some embodiments the jaws have a crescent or semi-circular jaw face which acts to form the adjacent strip of sheath material into a corresponding crescent or semi-circular shape against the stent being crimped.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
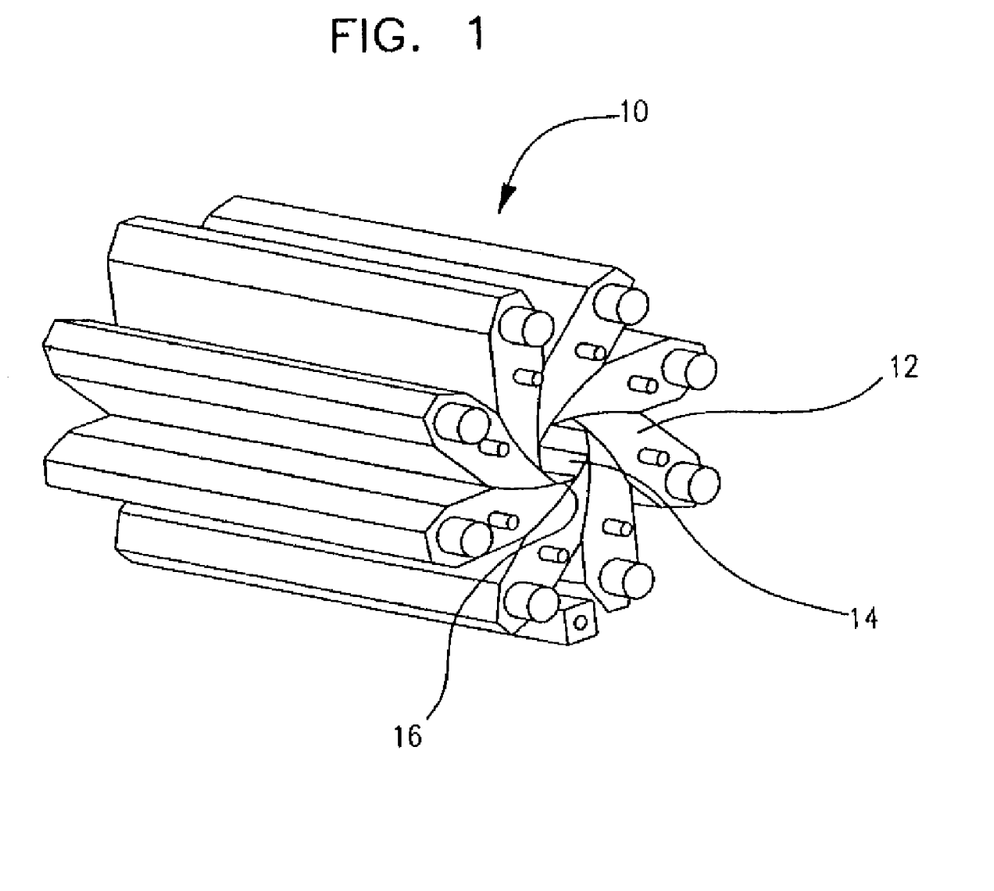
FIG. 1 is a perspective view an example stent crimper.

In some embodiments the present invention is directed to a system for reducing the diameter of a stent or crimping the stent onto a delivery catheter. In at least one embodiment a stent crimping system utilizes a stent crimper 10, an example of which is shown in FIG. 1. In the embodiment shown, the stent crimper 10 comprises a plurality of blades or crimping members 12, which define an iris 14.

Blades 12 may have any configuration or shape that may be desired and which is suitable for use in a crimping system. For example, the blades 12 in the embodiment shown in FIG. 1 have a curved edge 16, however in alternative embodiments the edge 16 of one or more blades 12 may be straight, curved, or provided with any of a variety of configurations.

Blades 12 are moveable between an open position and a closed position, such that when in the open position the iris defines a larger cross-sectional diameter, and in the closed position the diameter is reduced. The crimper 10 may be constructed to have an iris opening which is as large or as small as desired. In at least one embodiment, the diameter of the iris may range from 15 mm or more in the open position, such as is shown in FIG. 2, to as little as zero mm in the closed position, such as is shown in FIG. 3.

Figure 2:
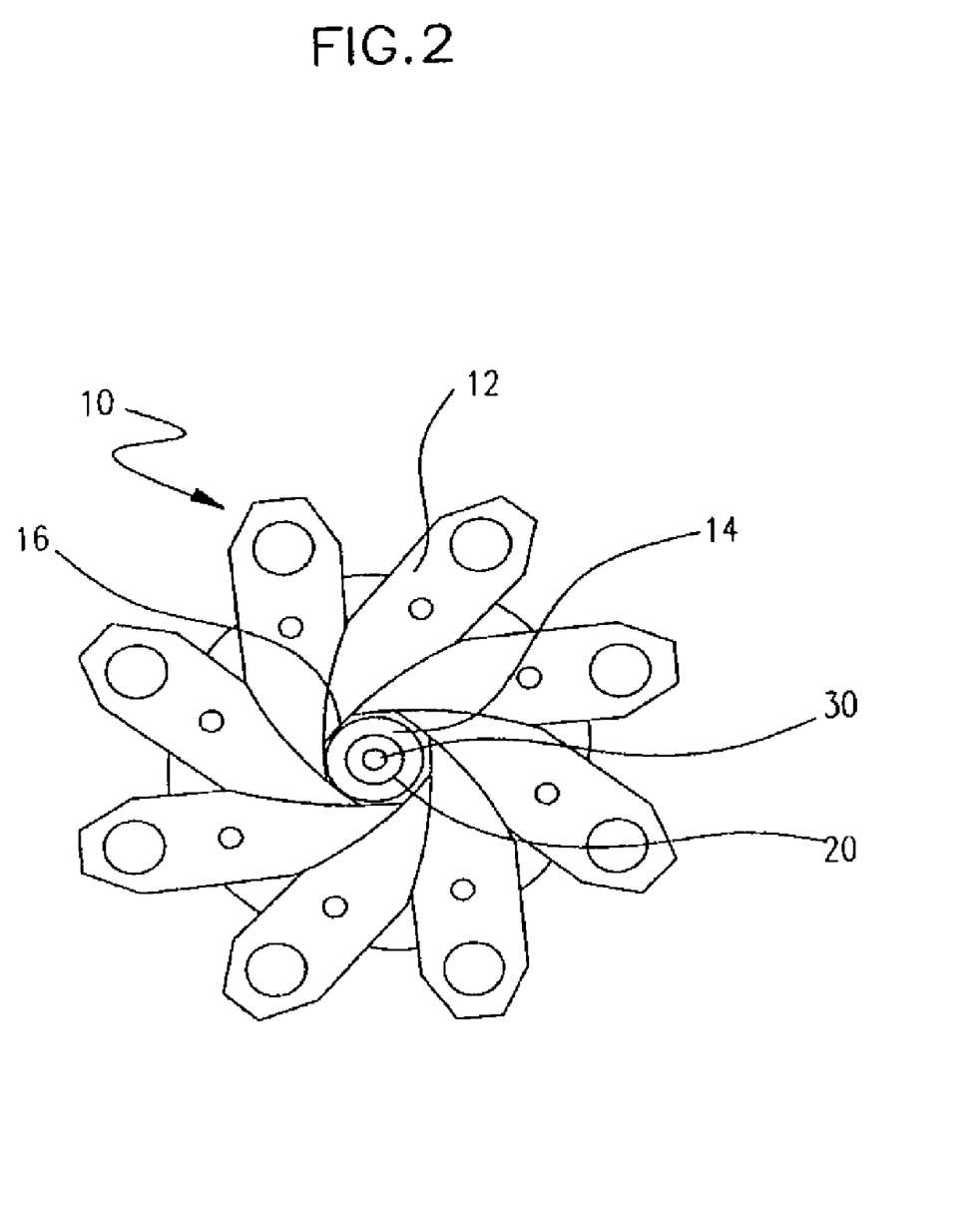
FIG. 2 is a cross-sectional view of the crimper shown in FIG. 1 with a stent delivery system positioned within the open iris.
Figure 3:
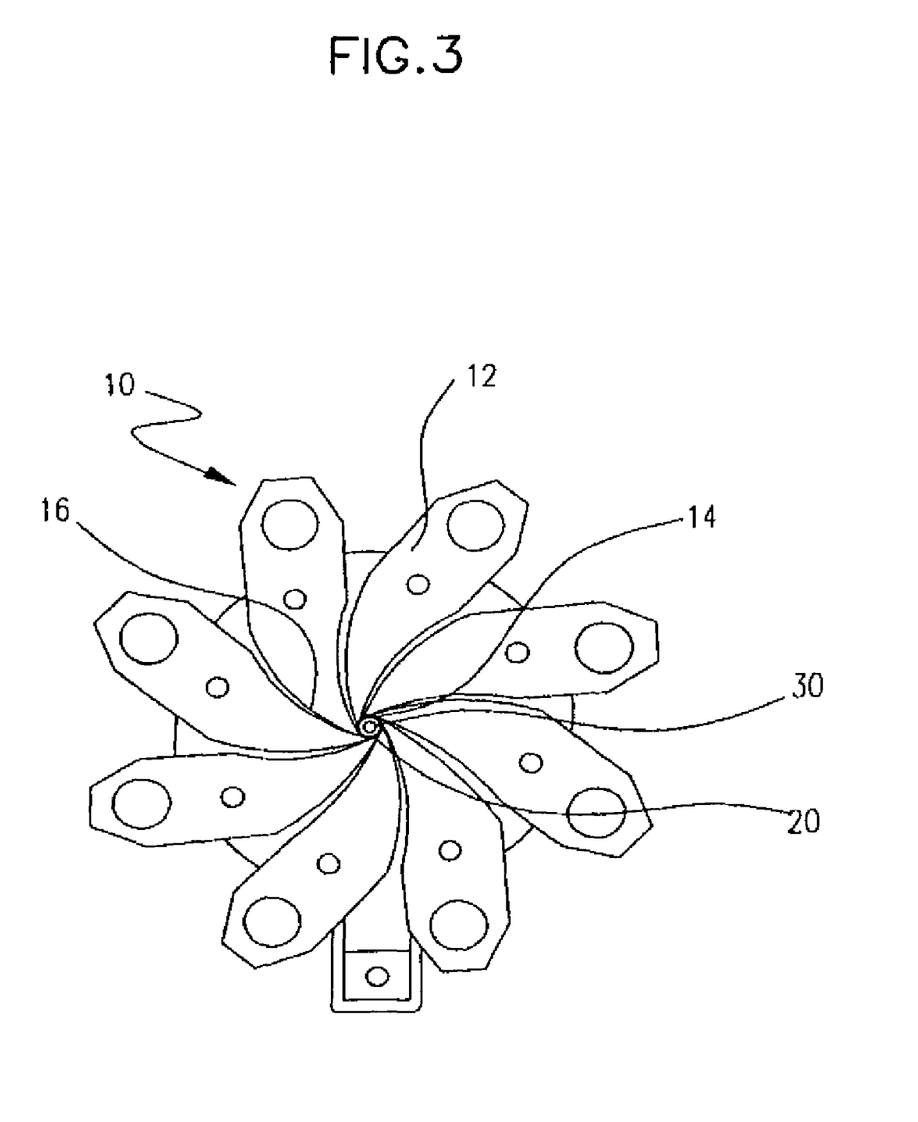
FIG. 3 is a cross-sectional view of the crimper shown in FIG. 1, wherein the iris is shown in the closed position

Regardless of the actual diameter or cross-sectional area (the iris need not be circular in cross-sectional shape, such as is shown) of the iris 14, in the open position the iris 14 is sized to accommodate the insertion of a stent 20 and/or a catheter assembly 30 such as in the manner shown in FIG. 2.

Figure 4:
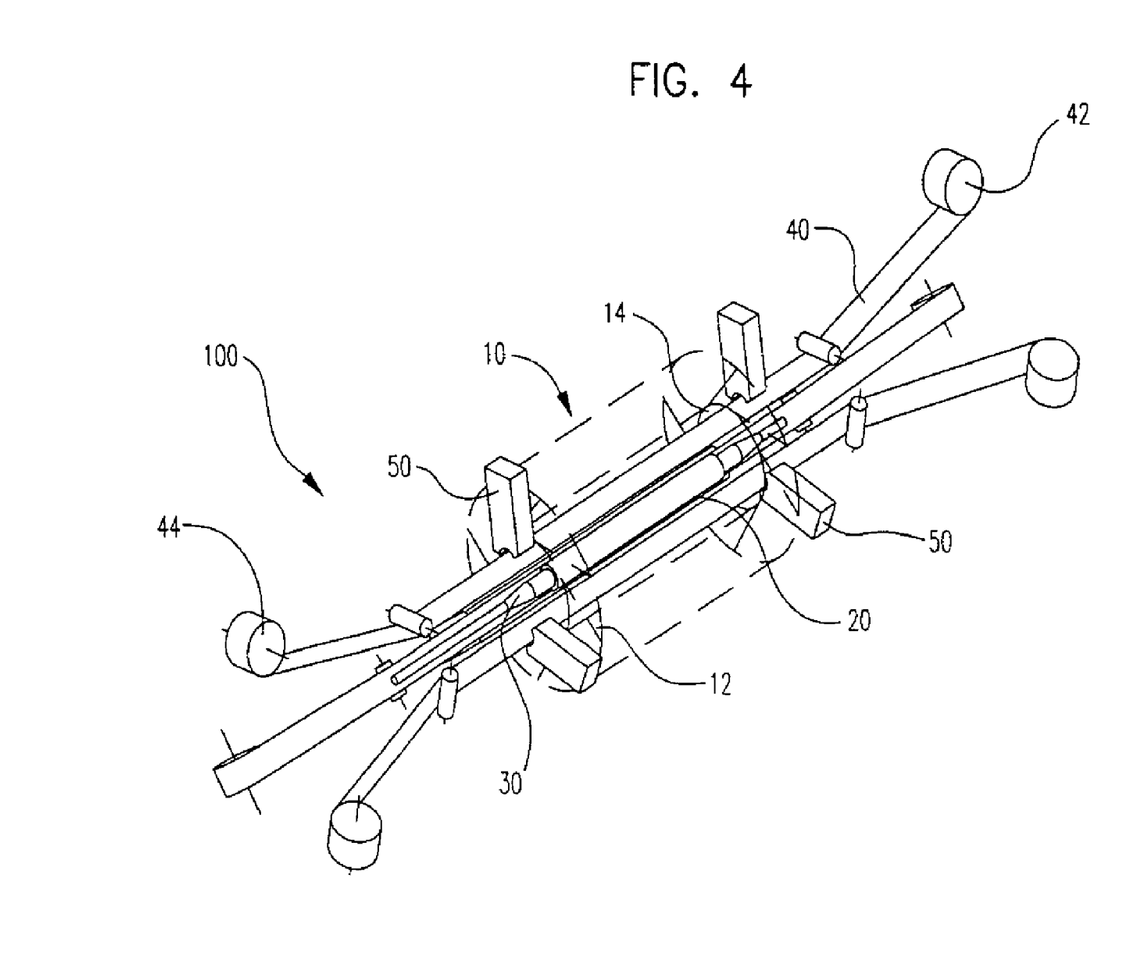
FIG. 4 is a perspective view of an embodiment of the invention wherein the crimping system is shown in the open or pre-crimped state.
Figure 6:
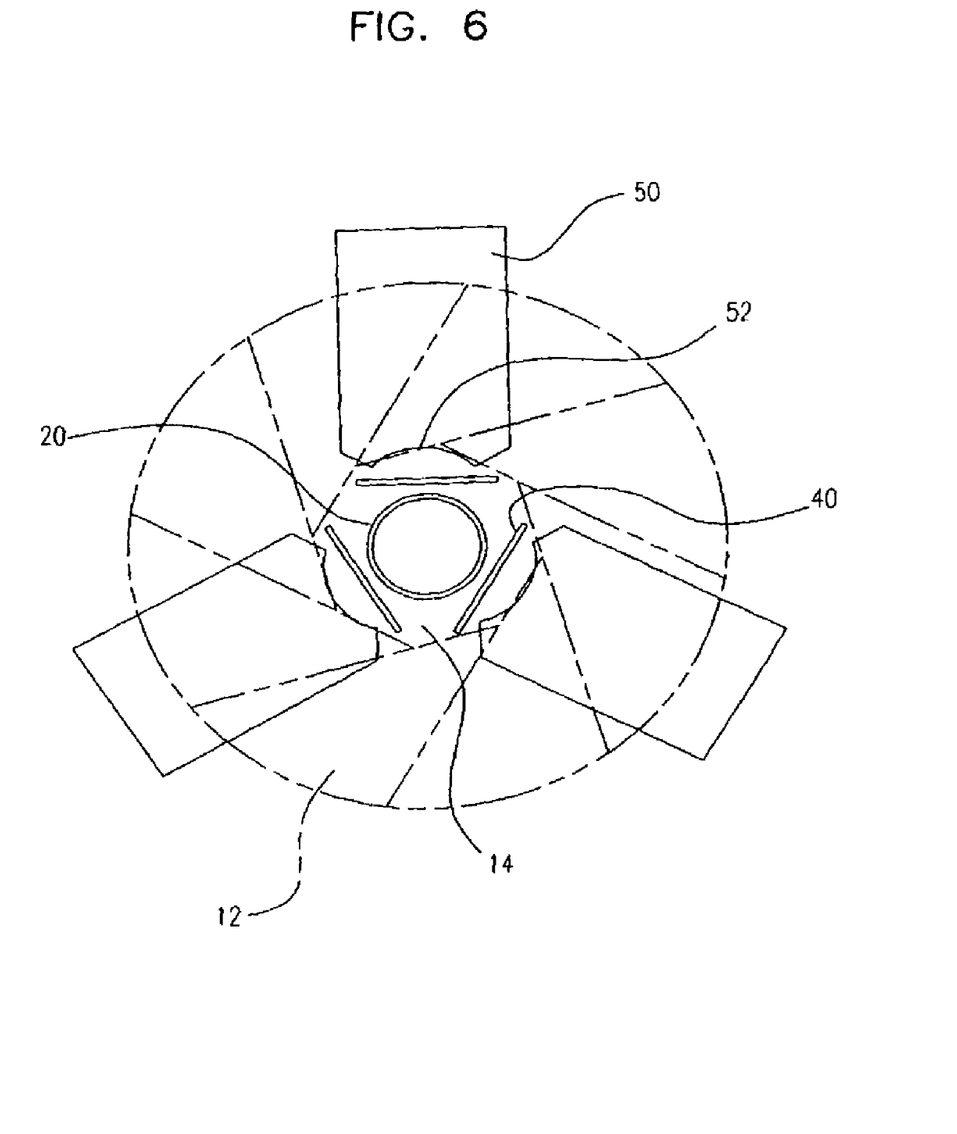
FIG. 6 is a cross-sectional view of a portion of the system shown in FIG. 4.
Figure 7:
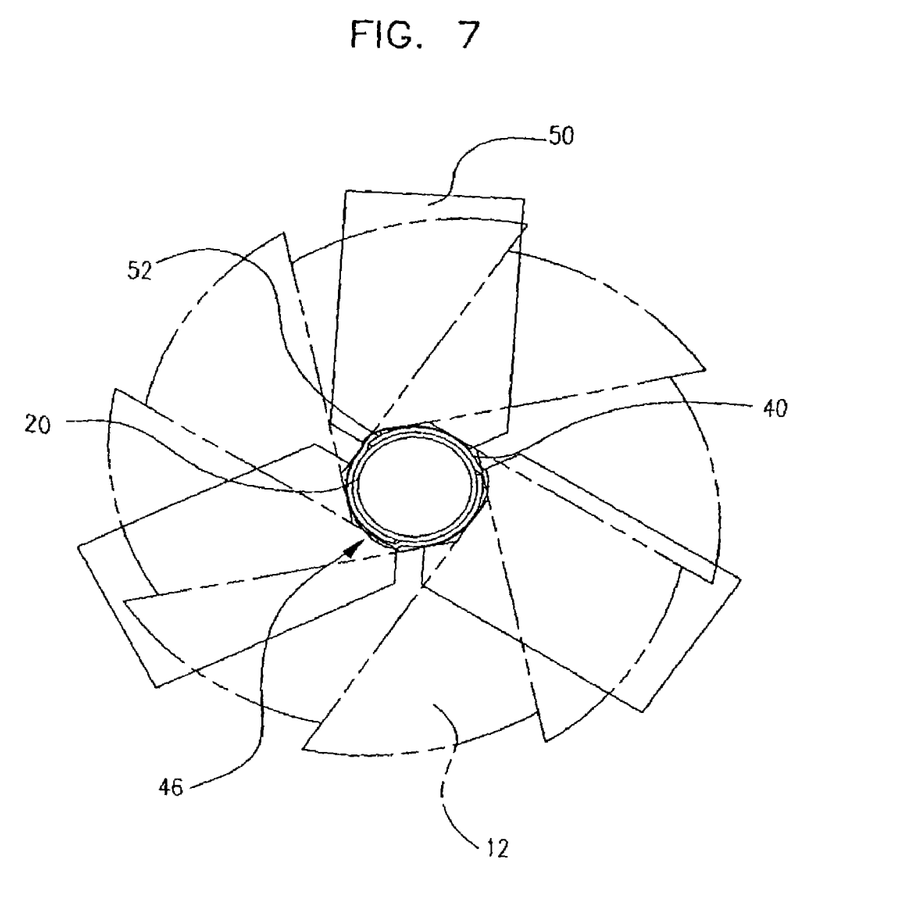
FIG. 7 is a cross-sectional view of a portion of the system shown in FIG. 5.

In a traditional crimping system, once the stent is properly positioned in the open iris, the blades of the crimper are actuated to move inward against the stent to reduce its diameter and, thereby crimp the stent to the catheter. As indicated above however, in some embodiments of the present invention, an example of which is shown in FIGS. 4 and 6, a plurality of strips 40 of protective material are positioned between the blades 12 of the crimper 10 and the stent 20. As the crimping blades 12 are moved radially inward toward the stent 20, the strips 40 are biased against the stent to provide a sheath-like layer 46 of protective material about stent 20, thereby preventing direct contact between the crimping blades 12 and the stent 20 such as is shown in FIGS. 5 and 7.

Strips 40 are particularly useful in protecting a stent 20 which has a coating or been otherwise preloaded with one or more therapeutic agents. In some embodiments stent 20 is provided with any of a variety of therapeutic agents, drugs or other pharmaceutical product(s) such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Strips 40 are characterized as a thin layer of protective polymeric material. Preferably the strips are constructed from a material which will not adhere to the stent 20 or detrimentally affect a therapeutic agent or agents associated with the stent. Some examples of suitable materials from which the strips can be manufactured include but are not limited to thermoplastic elastomers such as polyether block amides (PEBAX, etc.), polyamides such as KAPTON, etc.

Figure 5:
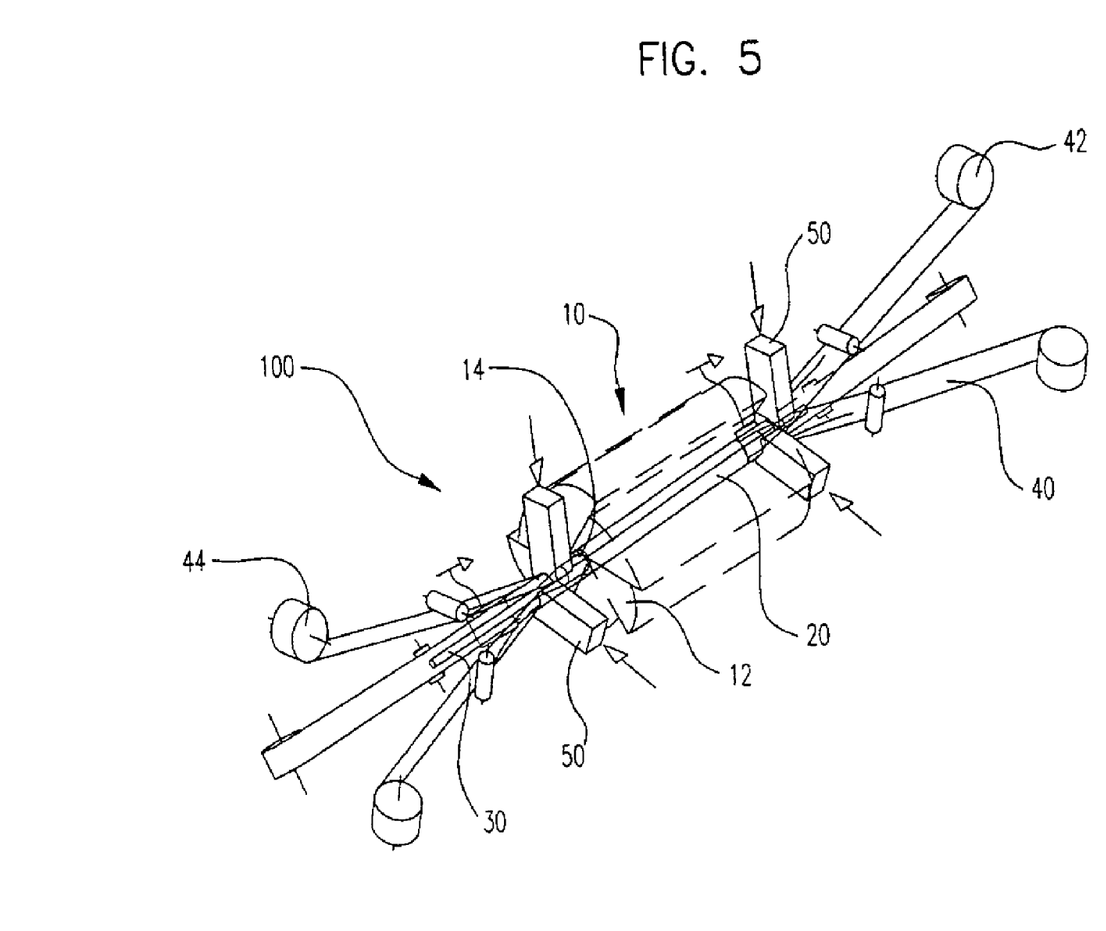
FIG. 5 is a perspective view of the embodiment shown in FIG. 4 wherein the system is shown in the closed or crimped state.

In the embodiment shown in FIGS. 4 and 5, each strip 40 is fed into, and extends through, the length of the iris 14. The strip 40 extends from a feeder spool 42 to receiver spool 44. Spools 42 and 44 may be any type of mechanism suitable for advancing and/or receiving a strip of protective material of the type described above. A feeder spool 42 is positioned adjacent to one end of the iris 14 with the receiver spool 44 positioned adjacent to the other end of the iris 14, with the strip 40 extending therebetween.

In some embodiments the spools 42 and 44 provide for an effectively continuous supply of strips 40 to the crimping iris. Following the crimping process of a given stent 20 the 'used' region of the strip 40 is drawn out of the iris 14 and into the receiver spool 44 while a new pre-crimped region of the strip 40 is advanced into positioned within the iris 14 and is subsequently ready to protect the next stent during crimping. The spools 42 and 44 can be configured to provide a strip having a plurality of iris lengths. Once the entire strip 40 has been used, the spent strip is replaced with a new strip as needed.

In FIGS. 4 and 5 a system 100 is shown wherein three strips 40 of protective material are spaced uniformly about the circumference of the stent 20. In the embodiment shown the strips 40 are tangentially offset about 120 degrees from one another. Alternative embodiments of the invention may utilize any number of spaced strips. For example, in at least one embodiment, only two strips 40, offset by about 180 degrees, are positioned about the stent. In at least one embodiment, four strips 40, offset by about 90 degrees, are positioned about the stent 20. Other embodiments may employ greater or lesser numbers of strips as desired.

As shown in FIGS. 4 and 5 strips 40 extend longitudinally through the crimping iris 14 throughout the crimping process. When the iris 14 is in the open position, such as is shown in FIG. 4, the strips 40 are spaced apart from one another and positioned between the blades 12 and the stent 20. As the iris is closed the strips 40 are biased radially inward toward the stent 20 and positioned around the contour of the stent 20 by one or more moveable plungers 50, such as in the manner shown in FIGS. 6 and 7. As shown, in FIGS. 4 and 5 each plunger 50 is positioned between an end of the iris 14 and a respective spool 42 or 44.

In at least one embodiment, an example of which is shown in FIGS. 6 and 7, the plungers 50 each define an engagement surface or jaw 52, which has a curved or concave surface which corresponds substantially to the external contour of the stent 20. As the strips 40 are pushed inward by engagement with the radially inward moving jaws 52, the shape of the individual jaw 52 will act upon a given strip 40 to bend the strip around the region of the stent 20 radially thereunder. If the strips are of sufficient width, the strips will overlap to effectively form sheath 46 about the stent 20, such as is depicted in FIG. 7.

As indicated above, in some embodiments different numbers of strips 40 maybe provided to the system 100. Similarly, in some embodiments strips 40 may be of different widths, of overlapping or non-overlapping configuration, may be constructed of similar or different materials, etc. Strips 40 can also be configured with surface features or other components such as bumps, hubs, cogs, etc., which for example, may be varied in position on adjacent strips to provide an interlocking function when the strips overlap to form sheath 46. In some embodiments strips 40 may be inherently lubricious and/or include one or more lubricious coatings on the stent side and/or blade side of a given strip. In at least one embodiment, strips 40 are provided with a multilayer construction such that one side of the strip has a greater durometer hardness than the other and/or other performance characteristics as desired.

In the embodiment shown in FIGS. 4-7 it should be noted that the strips 40 are independently moveable relative to one another in order to reduce or prevent occurrences of stent strut overlap during crimping.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent crimping system comprising:
   a crimping head including a plurality of crimping blades which collectively define an iris for receiving a stent therein, the iris defining an opening extending through the crimping head from a first end of the crimping head to a second end of the crimping head, the plurality of crimping blades being movable between an open position in which the opening of the iris has a first perimeter to a closed position in which the opening of the iris has a second perimeter less than the first perimeter;
   a first protective strip extending longitudinally through the opening of the iris of the crimping head from a feeder spool to a receiver spool, the first protective strip having a width measured from a first edge of the first protective strip to a second edge of the first protective strip opposite the first edge of the first protective strip; and
   a second protective strip extending longitudinally through the opening of the iris of the crimping head from a feeder spool to a receiver spool, the second protective strip having a width measured from a first edge of the second protective strip to a second edge of the second protective strip opposite the first edge of the second protective strip;
   wherein when the crimping blades are in the closed position, a first portion of the first protective strip overlaps a first portion of the second protective strip such that the first portion of the first protective strip is positioned between the stent and the first portion of the second protective strip, and the first portion of the second protective strip is positioned between the first portion of the first protective strip and the perimeter of the opening of the crimping iris.

2. The stent crimping system of claim 1, wherein the first portion of the first protective strip overlapping the first portion of the second protective strip is a curved portion of the first protective strip.

3. The stent crimping system of claim 2, wherein the first portion of the second protective strip overlapping the first portion of the first protective strip is a curved portion of the second protective strip.

4. The stent crimping system of claim 1, wherein when the crimping blades are in the closed position, the width of the first protective strip and the width of the second protective strip are both entirely radially inward of the perimeter of the opening of the iris.

5. The stent crimping system of claim 1, further comprising a third protective strip extending longitudinally through the opening of the iris of the crimping head from a feeder spool to a receiver spool, the third protective strip having a width measured from a first edge of the third protective strip to a second edge of the third protective strip opposite the first edge of the third protective strip.

6. The stent crimping system of claim 5, wherein when the crimping blades are in the closed position, a first portion of the third protective strip overlaps a second portion of the first protective strip and a second portion of the third protective strip overlaps a second portion of the second protective strip.

7. The stent crimping system of claim 6, wherein when the crimping blades are in the closed position, the first portion of the first protective strip is radially inward of the first portion of the second protective strip, the second portion of the second protective strip is radially inward of the second portion of the third protective strip, and the first portion of the third protective strip is radially inward of the second portion of the first protective strip.

8. A stent crimping system comprising:
a crimping head including a plurality of crimping blades which collectively define an iris for receiving a stent therein, the iris defining an opening extending through the crimping head from a first end of the crimping head to a second end of the crimping head, the plurality of crimping blades being movable between an open position in which the opening of the iris has a first perimeter to a closed position in which the opening of the iris has a second perimeter less than the first perimeter;
a first protective strip extending longitudinally through the opening of the iris of the crimping head from a feeder spool to a receiver spool, the first protective strip having a width measured from a first edge of the first protective strip to a second edge of the first protective strip opposite the first edge of the first protective strip; and
a second protective strip extending longitudinally through the opening of the iris of the crimping head from a feeder spool to a receiver spool, the second protective strip having a width measured from a first edge of the second protective strip to a second edge of the second protective strip opposite the first edge of the second protective strip;
wherein when the crimping blades are in the closed position, the width of the first protective strip and the width of the second protective strip are both completely within the perimeter of the opening of the iris of the crimping head.

9. The stent crimping system of claim 8, wherein when the crimping blades are in the closed position, the width of the first protective strip is curved from the first edge of the first protective strip to the second edge of the first protective strip.

10. The stent crimping system of claim 9, wherein when the crimping blades are in the closed position, the width of the second protective strip is curved from the first edge of the second protective strip to the second edge of the second protective strip.

11. The stent crimping system of claim 10, wherein a curved portion of the first protective strip overlaps a curved portion of the second protective strip.

12. The stent crimping system of claim 8, wherein when the crimping blades are in the open position, the width of the first protective strip and the width of the second protective strip are both completely within the perimeter of the opening of the iris of the crimping head.

13. The stent crimping system of claim 12, wherein when the crimping blades are in the open position, the width of the first protective strip is planar from the first edge of the first protective strip to the second edge of the first protective strip.

14. The stent crimping system of claim 13, wherein when the crimping blades are in the open position, the width of the second protective strip is planar from the first edge of the second protective strip to the second edge of the second protective strip.

15. A stent crimping system comprising:
a crimping head including a plurality of crimping blades which collectively define an iris for receiving a stent therein, the iris defining an opening extending through the crimping head from a first end of the crimping head to a second end of the crimping head, the plurality of crimping blades being movable between an open position in which the opening of the iris has a first perimeter to a closed position in which the opening of the iris has a second perimeter less than the first perimeter; and
a plurality of protective strips extending longitudinally through the opening of the iris of the crimping head from a feeder spool proximate the first end of the crimping head to a receiver spool proximate the second end of the crimping head, each of the plurality of strips being radially offset from one another around the perimeter of the opening of the iris, each protective strip having a width measured from a first edge of the protective strip to a second edge of the protective strip opposite the first edge of the protective strip;
wherein when the crimping blades are in the closed position, the entire width of each protective strip is positioned radially inward of the perimeter of the opening of the iris.

16. The stent crimping system of claim 15, wherein when the crimping blades are in the open position, the entire width of each protective strip is positioned radially inward of the perimeter of the opening of the iris.

17. The stent crimping system of claim 15, wherein a first portion of each protective strip overlaps a second portion of an adjacent protective strip when the crimping blades are in the closed position.

18. The stent crimping system of claim 17, wherein the first portion of each protective strip is a curved portion and the second portion is a curved portion.

19. The stent crimping system of claim 15, wherein the plurality of protective strips includes three protective strips arranged 120 degrees from one another.

* * * * *